United States Patent
Samuel et al.

(10) Patent No.: US 11,616,825 B2
(45) Date of Patent: Mar. 28, 2023

(54) SYSTEM AND METHOD OF AGGREGATING AND INTERPRETING DATA FROM CONNECTED DEVICES

(71) Applicant: Aetna Inc., Hartford, CT (US)

(72) Inventors: Robert Samuel, Blue Bell, PA (US); Sriram Ganesan, North Wales, PA (US)

(73) Assignee: Aetna Inc., Hartford, CT (US)

( * ) Notice: Subject to any disclaimer, the term of this patent is extended or adjusted under 35 U.S.C. 154(b) by 636 days.

(21) Appl. No.: 15/380,578

(22) Filed: Dec. 15, 2016

(65) Prior Publication Data

US 2017/0177798 A1 Jun. 22, 2017

Related U.S. Application Data

(60) Provisional application No. 62/269,576, filed on Dec. 18, 2015.

(51) Int. Cl.
*H04L 67/01* (2022.01)
*G06F 21/62* (2013.01)
(Continued)

(52) U.S. Cl.
CPC .......... *H04L 67/01* (2022.05); *G06F 21/6254* (2013.01); *G16H 10/65* (2018.01);
(Continued)

(58) Field of Classification Search
CPC .............. G06Q 50/22–24; H04L 67/42; H04L 67/12; G16H 10/65; G16H 80/00;
(Continued)

(56) References Cited

U.S. PATENT DOCUMENTS 6,041,357 A * 3/2000 Kunzelman ......... H04L 63/0815
709/228
7,260,837 B2 * 8/2007 Abraham ........... G06Q 20/3821
726/4
(Continued)

FOREIGN PATENT DOCUMENTS

WO WO-03034294 A2 * 4/2003 ............. G16H 10/65

OTHER PUBLICATIONS

Iwuchukwu, Anonymization Techniques for Large and Dynamic Data Sets, 2007, UMI/ProQuest, pp. 1-150. (Year: 2007).*

(Continued)

*Primary Examiner* — Joseph D Burgess
(74) *Attorney, Agent, or Firm* — Leydig, Voit & Mayer, Ltd.

(57) ABSTRACT

Embodiments of the disclosure provide a method for aggregating and providing health data records to an electronic device. The method is performed by a server that includes a processor and a non-transitory computer readable medium with processor-executable instructions stored thereon. When the instructions are executed by the processor, the server performs the method including: (a) receiving collected data from one or more client devices, the collected data comprising health related data including at least one of step count data, heart rate data, sleep sensor data; (b) extracting metadata from the collected data; (c) pseudonymizing the collected data; (d) categorizing the collected data using the extracted metadata and enterprise ontology of the server; and (e) storing the collected data.

20 Claims, 8 Drawing Sheets (51) Int. Cl.
  *H04L 67/12* (2022.01)
  *G16H 10/65* (2018.01)
  *G16H 80/00* (2018.01)
  *G16H 10/00* (2018.01)

(52) U.S. Cl.
  CPC ............. *H04L 67/12* (2013.01); *G16H 10/00* (2018.01); *G16H 80/00* (2018.01)

(58) Field of Classification Search
  CPC ........ G16H 10/60; G16H 50/70; G16H 15/00; G16H 40/67; G16H 50/30; G16H 20/00; G06F 21/6254; G06F 16/367; G06F 16/285; G06F 16/244; G06F 40/30; G06F 16/435; G06F 1/163; G06F 16/483; G06F 16/908
  See application file for complete search history.

(56) References Cited

U.S. PATENT DOCUMENTS

| | | | | |
|---|---|---|---|---|
| 7,978,062 | B2* | 7/2011 | LaLonde | A61N 1/37282 340/539.11 |
| 9,005,129 | B2* | 4/2015 | Venkatraman | A61B 5/721 600/500 |
| 2006/0136270 | A1* | 6/2006 | Morgan | G06F 17/2264 705/3 |
| 2007/0055552 | A1* | 3/2007 | St. Clair | G16H 50/20 705/3 |
| 2009/0192941 | A1* | 7/2009 | Fournier | G06F 19/328 705/51 |
| 2010/0235369 | A1* | 9/2010 | Evanitsky | G06Q 10/10 707/756 |
| 2011/0264809 | A1* | 10/2011 | Koster | G16H 10/60 709/227 |
| 2011/0288877 | A1* | 11/2011 | Ofek | G16H 50/20 707/661 |
| 2012/0239942 | A1* | 9/2012 | Yan | H04L 63/0421 713/189 |
| 2013/0111348 | A1* | 5/2013 | Gruber | G10L 15/26 715/727 |
| 2013/0291060 | A1* | 10/2013 | Moore | G16H 40/63 726/1 |
| 2015/0019553 | A1* | 1/2015 | Shaashua | G06N 7/005 707/737 |
| 2015/0379303 | A1* | 12/2015 | LaFever | G06F 21/6254 726/28 |
| 2016/0323247 | A1* | 11/2016 | Stein | H04L 63/0421 |
| 2017/0177798 | A1* | 6/2017 | Samuel | G06F 21/6254 |

OTHER PUBLICATIONS

Z. Deng, P. Yang, Y. Zhao, X. Zhao and F. Dong, "Life-Logging Data Aggregation Solution for Interdisciplinary Healthcare Research and Collaboration," 2015 IEEE International Conference on Computer and Information Technology; Ubiquitous Computing and Communications; (Year: 2015).*

Neubauer et al., *Int. J. Medical Informatics*, 80, 190-204 (2011).

IHE IT Infrastructure Technical Committee, *IHE IT Infrastructure Handbook: De-Identification*, © IHE International, Inc. (Mar. 14, 2014).

* cited by examiner

SYSTEM AND METHOD OF AGGREGATING AND INTERPRETING DATA FROM CONNECTED DEVICES

CROSS-REFERENCE TO RELATED APPLICATIONS

This patent application claims the benefit of U.S. Provisional Patent Application No. 62/269,576, filed Dec. 18, 2015, which is incorporated by reference in its entirety.

BACKGROUND

Electronic devices have been used in various aspects to enhance human comfort and increase productivity. The electronic devices range from general purpose computers to application specific devices, e.g., medical devices. The trend for electronic devices shows reduction in physical device size while improving device functionality. For example, a mobile phone today may exhibit multi-core processors and multiple communication radios in a form factor that could not be realized ten years ago and is able to perform more functions than mobile phones of its size ten years ago. As the scaling trend continues with smaller form factors, wearable electronic devices for various purposes have become common. Wearable devices include fitness trackers that monitor steps taken, heart rate and/or sleep patterns. Even though these devices have become common, they possess a wealth of potential, currently not being realized. As standalone devices, wearable devices are very limited. Many wearable devices are connected to the internet either though a smartphone or with built in wireless technology. Such devices become part of the internet of things (IoT).

BRIEF SUMMARY

Embodiments of the disclosure provide a method for aggregating and providing health data records to an electronic device. The method is performed by a server that includes a processor and a non-transitory computer readable medium with processor-executable instructions stored thereon. When the instructions are executed by the processor, the server performs the method including: (a) receiving collected data from one or more client devices, the collected data comprising health related data including at least one of step count data, heart rate data, sleep sensor data; (b) extracting metadata from the collected data; (c) pseudonymizing the collected data; (d) categorizing the collected data using the extracted metadata and enterprise ontology of the server; and (e) storing the collected data.

Embodiments of the disclosure also provide a server for aggregating and providing health data records to an electronic device. The server includes a processor and a non-transitory computer readable medium with processor-executable instructions stored thereon, such that when the instructions are executed by the processor, the server performs the method of: (a) receiving collected data from one or more client devices, the collected data comprising health related data including at least one of step count data, heart rate data, sleep sensor data; (b) extracting metadata from the collected data; (c) pseudonymizing the collected data; (d) categorizing the collected data using the extracted metadata and enterprise ontology of the server; and (e) storing the collected data.

Embodiments of the disclosure further provide a non-transitory computer-readable medium for aggregating and providing health data records to an electronic device. The non-transitory computer-readable medium stores processor-executable instructions for performing the method of: (a) receiving collected data from one or more client devices, the collected data comprising health related data including at least one of step count data, heart rate data, sleep sensor data; (b) extracting metadata from the collected data; (c) pseudonymizing the collected data; (d) categorizing the collected data using the extracted metadata and enterprise ontology of the server; and (e) storing the collected data.

DETAILED DESCRIPTION

Current tools and techniques for extracting member, constituent, or patient data from connected devices and securely ingesting into enterprise databases lack comprehensive solutions in regards to protecting member-identifiable data without exposing data to security threats. Current tools also lack provisions for dynamically mapping the contents from various connected devices to enterprise ontology/taxonomy thereby providing semantic linkage of new contents arriving from disparate connected devices to enterprise contents.

Embodiments of the disclosure describe a system for collecting data, analyzing the data, and visualizing the implications of the analyzed data. In some embodiments, the data is collected from disparate sources, for example, electronic devices like heart rate monitors, blood sugar monitors, step counters, global positioning system (GPS) devices, etc. After collecting data, the system analyzes the data and provides a visual output that a user may view on an electronic device. This system may be applied in various environments, but for ease of explanation, the healthcare environment will be used as an example. As methods of collecting data continue to expand, the advent of the internet of things (IoT) will provide even more devices and sensors for data collection. As such, this system will integrate data from the multiple IoT devices and other non-IoT sources and provide insightful information to a healthcare provider or a patient (constituent) regarding the condition of the patient. Instead of these devices operating in an environment alone, embodiments of the disclosure provide a system that integrates, aggregates, secures, and associates information between multiple devices using various algorithms, personalization and healthcare semantic information.

Embodiments of the disclosure further provide a holistic approach for (1) identifying and securely ingesting member, constituent, or patient data coming from various IoT devices into a persistent container or database for long-term storage and analysis; (2) decoupling and pseudonymizing member-identifiable data and intelligently applying de-identification algorithms on various types of member-identifiable data coming from the IoT devices for various types of access; and (3) mapping semantics of the data coming from the IoT devices to appropriate enterprise ontological schema. Enterprise ontological schema or taxonomy is a method of organizing data according to a meaning ascribed to the data by the enterprise system. For example, an enterprise system may store birthdates, social security numbers, and member names as unstructured data.

Figure 1:
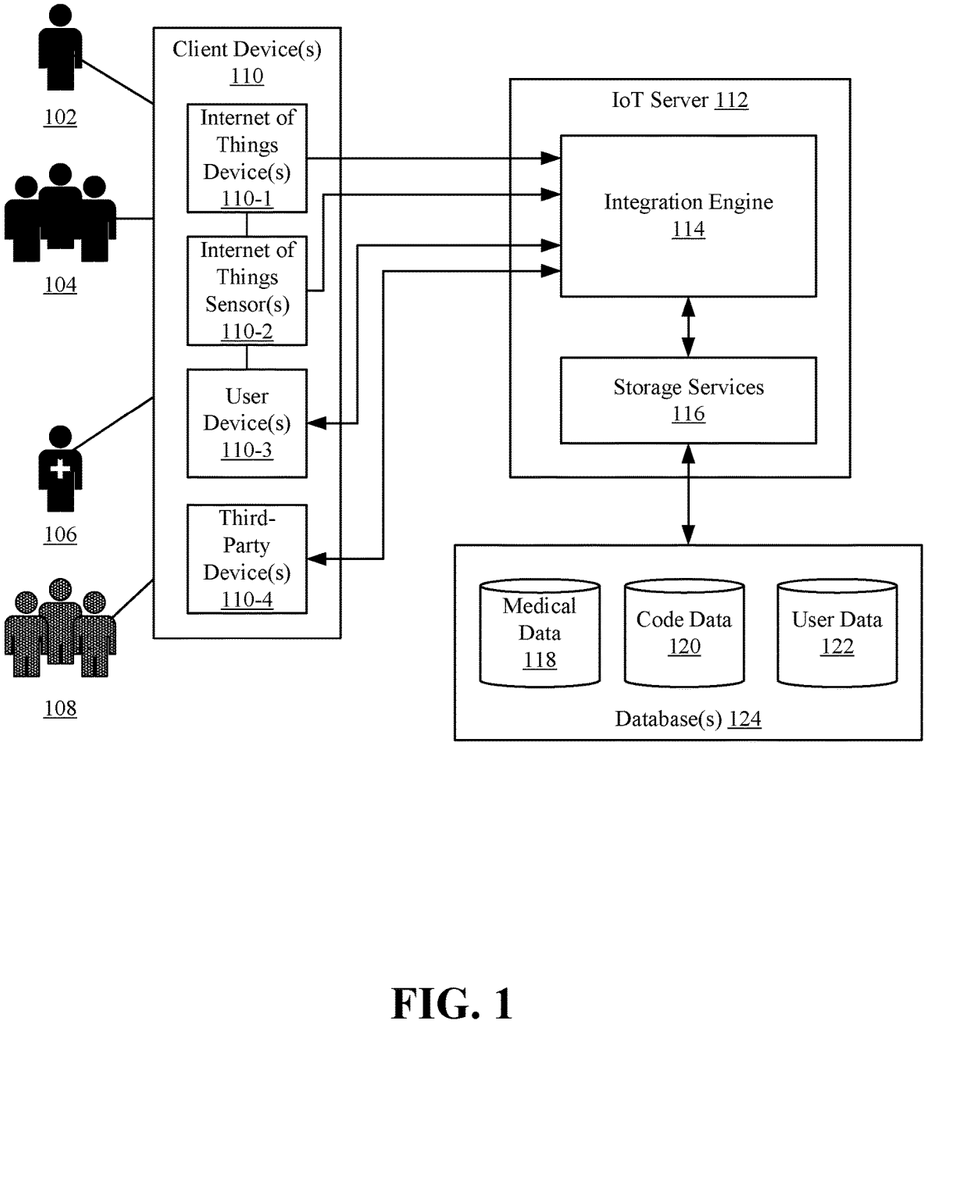
FIG. 1 shows a system level diagram illustrating an architecture for aggregating and accessing aggregated data from connected devices according to an embodiment of the disclosure.

FIG. 1 provides a system level diagram illustrating an architecture for aggregating and accessing aggregated data from connected or client devices 110 according to an embodiment of the disclosure. Client devices 110 used by one or more users (identified as items 102, 104, 106, and 108 in FIG. 1) interface with IoT server 112 with an external database 124. The IoT server 112 collects user data from IoT sensors and devices, integrates the user data in the integration engine 114, stores the data in database 124, and makes the data easily accessible to client devices 110 upon proper authentication.

Client devices 110 includes IoT devices 110-1, IoT sensors 110-2, user devices 110-3, and third-party devices 110-4. These categories under client devices 110 are macro categories to cover devices that may be used by a patient or user 102, individuals authorized by the user (authorized users 104), healthcare provider 106, and secondary parties 108. The patient or user 102 is identified as the subject of the data being monitored by the IoT devices 110-1 and IoT sensors 110-2. Devices used by others (not the patient) to interface with the IoT server 112 are identified as third-party devices 110-4.

User 102 may also have other devices identified as user devices 110-3. In some cases, the IoT devices 110-1, IoT sensors 110-2, and user devices 110-3 are communicably coupled to one another. For example, IoT sensors 110-2 may include a global positioning service (GPS) receiver and a gyroscope which are integrated in an IoT device 110-1 which may be a fitness tracker with Bluetooth® connectivity. The fitness tracker may then communicate with and transfer data to a user device 110-3 which may be a smartphone belonging to user 102. As such, the IoT sensors 110-2 are integrated to provide information to an IoT device 110-1 which uses a user device 110-3 as a means to interface with IoT server 112. In some embodiments, as shown in FIG. 1, each of IoT devices 110-1, IoT sensors 110-2, and user devices 110-3 may be configured to interact directly with IoT server 112. User device 110-3 also provides a means for bidirectional information transfer between user device 110-3 and IoT server 112. For example, user device 110-3 may provide fitness tracking data to IoT server 112, and IoT server 112 may analyze the fitness tracking data and provide graphical results to user device 110-3.

The patient or user 102 may want some of their information available to others or for public use. In some cases, there are different levels of access possible depending on who wants access to information of user 102. When authorized users 104 access the information of user 102 using third-party devices 110-4, IoT server 112 will have a certain level of security protocols appropriate. Thus, in some embodiments, user 102 can provide different level of information access to family members and friends who are authorized users 104. A physician or healthcare provider 106 may have a different security level and therefore able to access more information for the care of the patient or user 102. Secondary parties 108 may further have less security clearance for information relating to the patient or user 102. Secondary parties 108 include researchers, universities, etc. Examples of client devices 110 include smartphones, fitness trackers that measure heart rate, sleep patterns, steps taken, laptop computers, remote patient monitoring devices connected to the internet, personal/wearable devices include wellness and medical wearables from heart rate monitor, atrial fibrillation monitor, to insulin monitor and body temperature monitor.

IoT server 112 includes an integration engine 114 and a storage services 116. The integration engine 114 is responsible for receiving IoT data from client devices 110 and running application programming interfaces (APIs) to receive inputs and provide outputs to client devices 110. Storage services 116 receive the IoT data from the integration engine 114 and prepares the data for storage in database 124. The preparation for storage involves applying masking algorithms, semantic algorithms, and encryption algorithms to the data. Furthermore, when sending information from IoT server 112 to client devices 110, storage services 116 retrieves information from database 124 and provides the information to the integration engine 114.

Database 124 stores various data and parameters. For example, several algorithm parameters and rules may be stored in database 124. Database 124 may hold medical data 118 which is the medical record of user 102. Database 124 may also hold user data 22 which is related to IoT data obtained from client devices 110. Database 124 may also hold code data 120 which is data that relates the medical data 118 to the user data 122. Database 124 is provided as a generalization of an enterprise container, storing medical data 118, user data 122, and code data 120 with an ontological schema based on metadata present within each of the medical data 118 and user data 122.

Figure 2:
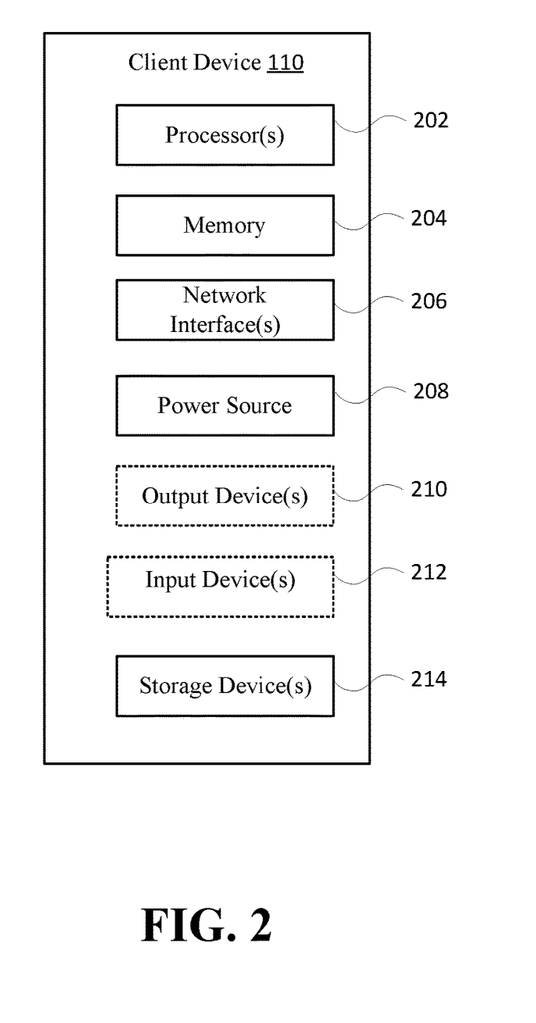
FIG. 2 illustrates components of a client device according to some embodiments of the disclosure.

FIG. 2 illustrates a block diagram of the basic hardware components for the client device 110 according to some aspects of the disclosure. The client device 110 may include one or more processors 202, memory 204, network interfaces 206, power source 208, output devices 210, input devices 212, and storage devices 214. Although not explicitly shown in FIG. 2, each component provided is interconnected physically, communicatively, and/or operatively for inter-component communications in order to realize functionality ascribed to the client device 110. To simplify the discussion, the singular form will be used for all components identified in FIG. 2 when appropriate, but the use of the singular does not limit the discussion to only one of each component. For example, multiple processors may implement functionality attributed to processor 202.

Processor 202 is configured to implement functions and/or process instructions for execution within client device 110. For example, processor 202 executes instructions stored in memory 204 or instructions stored on a storage device 214. In certain embodiments, instructions stored on storage device 214 are transferred to memory 204 for execution at processor 202. Memory 204, which may be a non-transient, computer-readable storage medium, is configured to store information within client device 110 during operation. In some embodiments, memory 204 includes a temporary memory that does not retain information stored when the client device 110 is turned off. Examples of such temporary memory include volatile memories such as random access memories (RAM), dynamic random access memories (DRAM), and static random access memories (SRAM). Memory 204 also maintains program instructions for execution by the processor 202 and serves as a conduit for other storage devices (internal or external) coupled to client device 110 to gain access to processor 202.

Storage device 214 includes one or more non-transient computer-readable storage media. Storage device 214 is provided to store larger amounts of information than memory 204, and in some instances, configured for long-term storage of information. In some embodiments, the storage device 214 includes non-volatile storage elements. Non-limiting examples of non-volatile storage elements include floppy discs, flash memories, magnetic hard discs, optical discs, solid state drives, or forms of electrically programmable memories (EPROM) or electrically erasable and programmable (EEPROM) memories.

Network interfaces 206 are used to communicate with external devices and/or servers. The client device 110 may comprise multiple network interfaces 206 to facilitate communication via multiple types of networks. Network interfaces 206 may comprise network interface cards, such as Ethernet cards, optical transceivers, radio frequency transceivers, or any other type of device that can send and receive information. Non-limiting examples of network interfaces 206 include radios compatible with several Wi-Fi standards, 3G, 4G, Long-Term Evolution (LTE), Bluetooth®, etc.

Power source 208 provides power to client device 110. For example, client device 110 may be battery powered through rechargeable or non-rechargeable batteries utilizing nickel-cadmium or other suitable material. Power source 208 may include a regulator for regulating power from the power grid in the case of a device plugged into a wall outlet, and in some devices, power source 208 may utilize energy scavenging of ubiquitous radio frequency (RF) signals to provide power to client device 110.

Client device 110 may also be equipped with one or more output devices 210. Output device 210 is configured to provide output to a user using tactile, audio, and/or video information. Examples of output device 210 may include a display (cathode ray tube (CRT) display, liquid crystal display (LCD) display, LCD/light emitting diode (LED) display, organic LED display, etc.), a sound card, a video graphics adapter card, speakers, magnetics, or any other type of device that may generate an output intelligible to user 104.

Client device 110 may be equipped with one or more input devices 212. Input devices 212 are configured to receive input from user 104 or the environment where client device 110 resides. In certain instances, input devices 212 include devices that provide interaction with the environment through tactile, audio, and/or video feedback. These may include a presence-sensitive screen or a touch-sensitive screen, a mouse, a keyboard, a video camera, microphone, a voice responsive system, or any other type of input device.

The hardware components described thus far for client device 110 are functionally and communicatively coupled to achieve certain behaviors. In some embodiments, these behaviors are controlled by software running on an operating system of client device 110.

Figure 3:
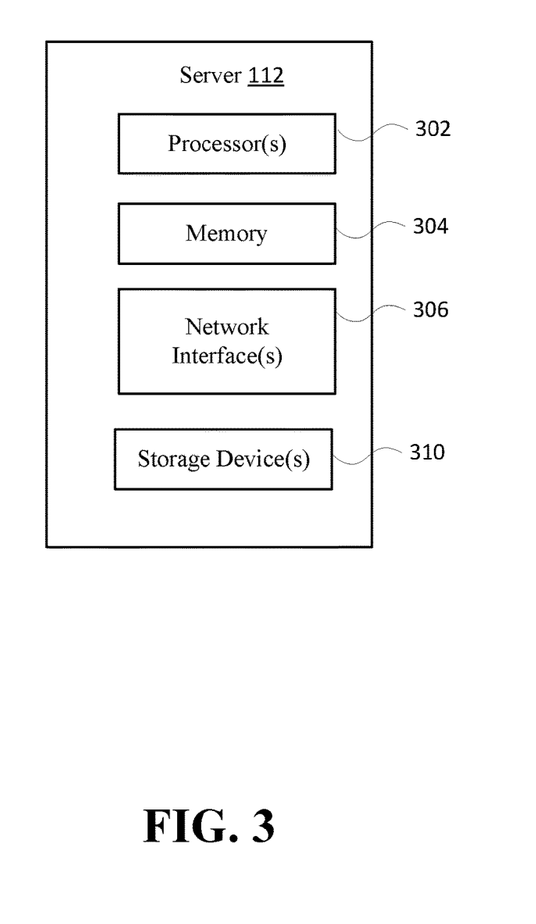
FIG. 3 illustrates components of a server according to some embodiments of the disclosure.

In FIG. 3, a block diagram of server 112 is provided with exemplary components. The behavior, function, and description of the various components are analogous to those already described for client device 110. For example, server 112 may include one or more processors 302, memory 304, network interfaces 306, and storage devices 310. The description for these components will not be provided, but it is understood that examples of these components may include those already provided for client device 110.

Figure 4:
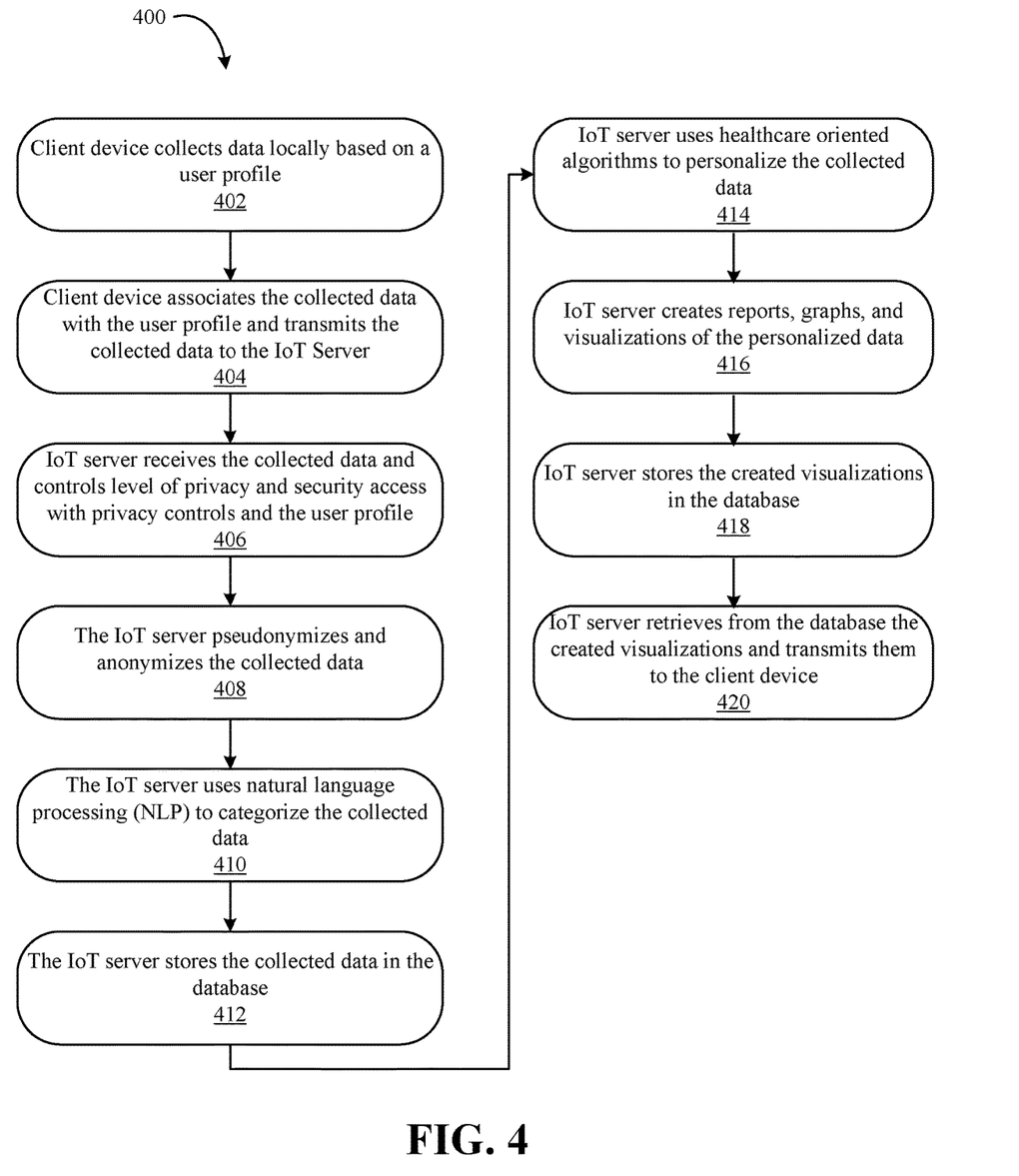
FIG. 4 shows an exemplary flow diagram illustrating the steps of collecting data from multiple sources and providing a visual output to a user according to an embodiment of the disclosure.

FIG. 4 shows an exemplary flow diagram illustrating a process 400 of collecting data from multiple sources and providing a visual output to a user according to an embodiment of the disclosure. At step 402, the process begins with client device 110 collecting constituent, patient, or user 102 health-oriented data. Constituent health oriented data is securely collected locally to the user through IoT sensors 110-2, sensors on IoT devices 110-1, or sensors on user device 110-3 based on a constituent or user profile. For example, the data may be collected through a myriad of wearable devices like smart watches or smart phones with accelerometers to decipher the number of steps the patient or constituent takes. In other examples, a heart-rate monitor collects heart-rate data and provides such data to the constituent's smart phone or data hub. Other sensors and devices may be used in the system of FIG. 1, for example, respiration rate monitor, temperature sensor, skin moisture sensor, electrophysiological signal sensors for electroencephalography (EEG) and/or electrocardiogram (EKG) signals, sleep sensors, stretch sensors that measure posture and swelling and other physical displacements, rehabilitation sensors like wireless sensor insoles, muscle contractor sensors, etc. In addition, data may be collected from multiple software platforms running on third-party devices 110-4, for example, medical records, claims data, social network data, etc. Health-oriented data can be collected from the constituent or patient, insurers and/or medical providers.

At step 404, the client device 110 associates the collected data with the profile of user 102 and securely transmits the collected data to the IoT server 112. In some embodiments, the collected data is transmitted in real-time as data is being collected. In other embodiments, the collected data is transmitted in bulk at a scheduled time. Some examples may institute thresholding so data is transmitted in bulk when a certain amount of data is collected, that is, when a certain data threshold is reached. Some examples may institute time thresholding so data is transmitted in bulk when a certain amount of time has elapsed. In some embodiments, data is gathered from cloud-based applications such as Fitbit® server or from an intermediary who consolidates IoT data from multiple vendors.

At step 406, the integration engine 114 of the IoT server 112 receives the collected data and automatically controls the level of privacy, security access, and data level details with privacy controls settings and the profile of user 102.

At step 408, the integration engine 114 provides the collected data to the storage services 116 for pseudonymization and anonymization. The storage services 116 applies predetermined algorithms and models to the data for pseudonymization and anonymization of key identifiers. In some embodiments, healthcare data is protected under privacy laws, so at step 408 constituent identity information is removed from the collected data. In another embodiment, as key identifiers are removed from the collected data, the data is tokenized to be able to group certain data together. By applying tokens, the storage services 116 is able to group certain set of data collected from one user. In the event that the storage services 116 is processing collected data or collected health data pertaining to more than one user, associating collected data with tokens allows keeping user data separate and avoiding associating one individual's data with another individual's data.

At step 410, the storage services 116 uses natural language processing (NLP) to categorize the pseudonymized collected data. To transform Data to Information, various algorithms are applied by computing systems to the tokenized data using healthcare information. For example, algorithms with semantic understanding of healthcare taxonomy enhanced with other healthcare information coming from diary notes, medical records, lab results, food logs, doctor's notes, nutritionist data, claims data, sleep data, etc. are applied to the tokenized data. Healthcare specific patterns using principles around linked data, graphs, ontology and taxonomies are applied. Additionally, in this step, healthcare specific patterns for categorization, auto-classification and tagging are applied. It is understood that certain algorithms are chosen based on the nature of the tokenized data and the additional data, like doctor's notes obtained from other sources.

At step 412, the storage services 116 stores the collected data in database 124. In some embodiments, secure data is encrypted and stored in the database 124. In certain implementations, the database 124 may contain policies and rules for interpreting the encrypted and stored data as linked information. The database 124 may also include a semantics graph storage with active analytics to provide information quickly upon receiving requests from storage services 116.

At step 414, the storage services 116 uses healthcare oriented algorithms to personalize the collected data based on the profile of user 102. That is, healthcare oriented algorithms based on the constituent profile are calculated by the storage services 116. This step involves personalizing the information based on the profile of user 102 (or constituent profile). In some examples, the user or constituent may only prefer a certain level of detail, and the analytics system may take that into consideration. In some instances, the constituent has not traveled to a region with certain diseases so the analytics system will take that into account as well. Step 414 involves using healthcare models and algorithms along with constituent profile to make the categorized data of step 410 more relevant to the constituent.

At step 416, the storage services 116 systematically creates reports, graphs, and visualizations for electronic delivery to the client device 110 (or for displaying on a constituent's device or user device 110-3). In some embodiments, an open source format, e.g., scalable vector graphics (SVG), is chosen for visualization in order to increase compatibility with a wider range of electronic devices such as smartphones.

At step 418, the storage services 116 sends the created health-oriented reports, graphs and visualizations to the database 124 for storage based on data management rules.

At step 420, the integration engine 114 invokes the storage services 116 to retrieve from the database 124 the created visualizations and transmit the visualizations to the client device 110.

Process 400 includes steps of collecting IoT data at client device 110 and packaging and transmitting the IoT data to the IoT server 112. IoT server 112 then prepares the collected data by pseudonymizing and anonymizing the collected data and categorizing the pseudonymized data. Database 124 then stores the pseudonymized data and using healthcare oriented algorithms along with user preferences included in a constituent's or user profile, connects the pseudonymized data to a broader range of information already known about the constituent or user. During this process, the IoT server 112 creates reports and other visualizations and stores them in the database 124. Upon request from one or more client device(s) 110, the IoT server 112 retrieves from the database 124 the visualizations and transmits them to the client device(s) 110. The secure data ingestion (steps 406 and 408) and the semantic storage of the data (steps 410 and 412) will be further explained using the flow diagram in FIG. 5.

Figure 5:
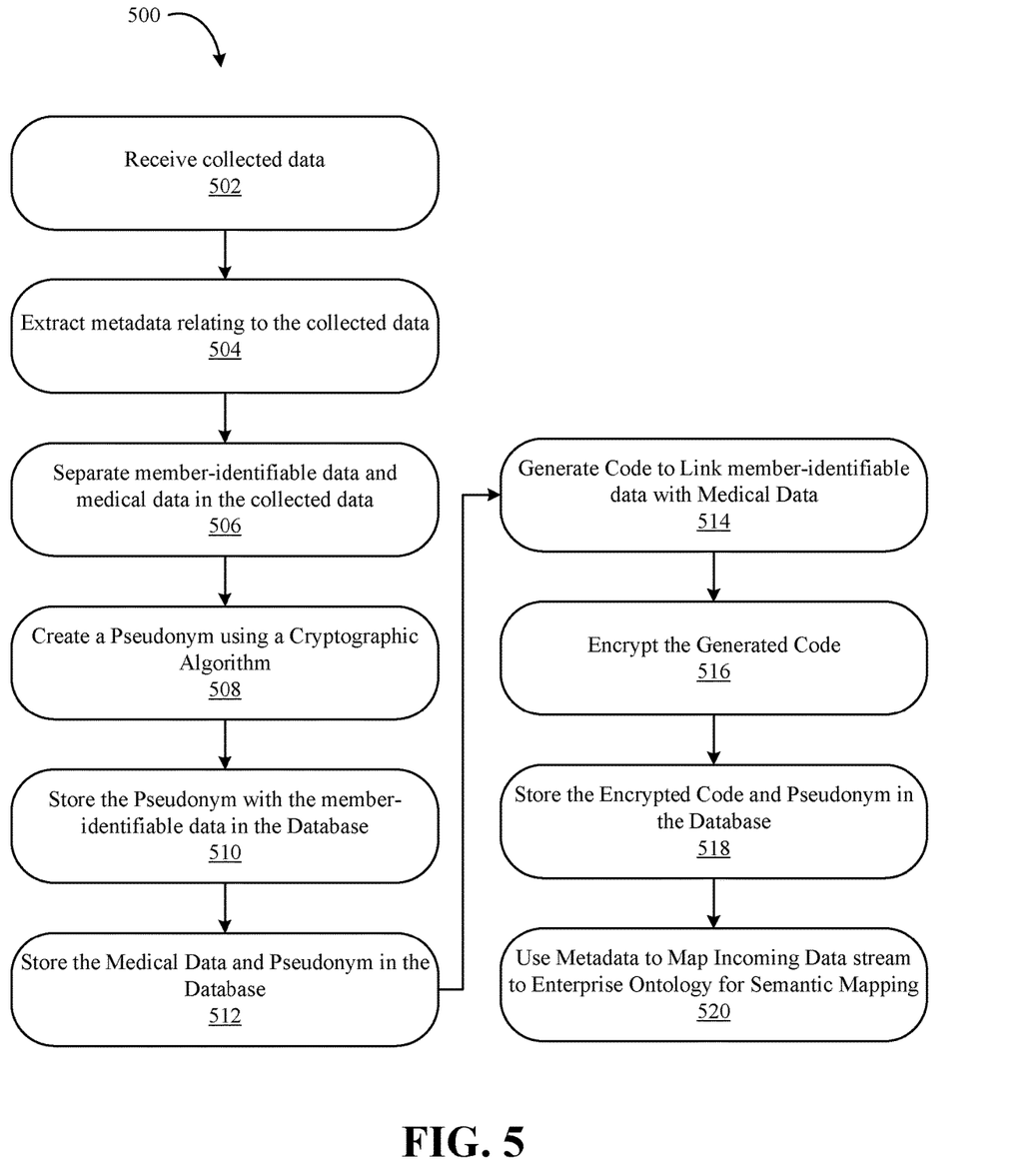
FIG. 5 shows a flow diagram illustrating the steps of collecting data and storing data in a database according to an embodiment of the disclosure.

FIG. 5 shows a flow diagram illustrating the steps of receiving collected data from one or more client device(s) 100 and storing the collected data in the database 124 according to an embodiment of the disclosure. Steps 502 and 504 relate to step 406; steps 506 and 508 relate to step 408; steps 510, 512, 514, 516, and 518 relate to step 412; and step 520 relates to step 410. At step 502, the integration engine 114 receives the collected data from the client device(s) 110.

At step 504, the integration engine extracts metadata relating to the collected data. In some embodiments, the collected data has various identifying fields to make sense of values or expressions in the collected data. These identifying fields may include a constituent's or user's date of birth, zip code, location, social security number, member identification (ID), address, etc. Additionally, the member's preferences, access permissions, and privacy controls are received as well.

At step 506, based on the extracted metadata, the storage services 116 separates member-identifiable data and medical data in the collected data. Member-identifiable data include protected health information (PHI) and personal identifiable information (PII) while medical data include actual medical records as images and/or text. Medical data may include, for example, doctor notes, clinical notes, diagnostic results, vital sign readings, radiology images, and so on. If the storage services 116 identifies any PHI or PII elements in the collected data, member-identifiable and medical data in the collected data are separated. PHI elements are identified in the Health Insurance Portability and Accountability Act (HIPAA) as items that should be removed to establish that health information is not individually identifiable. These include, for example, names, geographic subdivisions, dates, telephone numbers, fax numbers, e-mail addresses, biometric identifiers, device identifiers and serial numbers, SSN, internet protocol address, health plan beneficiary numbers, full-face photographs, account numbers, etc. PII elements include personal information that may be found beyond an individual's health record but may identify the individual. These include, for example, driver's license number, credit card numbers, criminal record, vehicle registration plate number, birth place, digital identity, login name, nickname, etc. Note that some elements are shared between the PHI and PII groupings, for example, both groupings include home address, names, e-mail address, SSN, etc.

At step 508, the storage services 116 creates a pseudonym or token using a cryptographic algorithm and prepares the pseudonym for storage. The storage services 116 may choose a pseudonym at random, may use the MD5, SHA-1 (Secure Hash Algorithm 1), or any other hash function to generate a hash value and use the hash value as the pseudonym. In some cases, contents from the constituent's or user's profile are utilized in creating the pseudonym. For example, the storage services 116 may create a pseudonym using symmetric key algorithm on a member ID of the user 102 if the member ID is present the profile of user 102. After creating the pseudonym, in order to prepare the pseudonym for storage, the storage services 116 encrypts the pseudonym and creates a map function to access member-identifiable data through the pseudonym.

At step 510, the storage services 116 stores the pseudonym with the member-identifiable data in the database 124 as user data 122. Alongside the pseudonym and member-identifiable data, the storage services 116 also stores the map function created at step 508 as user data 122.

At step 512, the storage services 116 then stores the medical data separated at step 506 in the database 124 as medical data 118.

At step 514, the storage services 116 then generates a code to link the stored member-identifiable data (user data 122) and the stored medical data (medical data 118). For example, the code may be generated using the format <Device Type><Device ID if available><Document Type><Disease or Diagnostic Code Identifier><Timestamp>. Devices may be identified by type or identification serial. Document type is the type of data the code links to, for example, text or image. Disease or Diagnostic Code Identifier may include, for example, ICD-10 (10th revision of the International Statistical Classification of Diseases and Related Health Problems). Timestamp is the time the data was collected.

At step 516, the storage services 116 then encrypts the generated code, for example, using well-known encryption methods including symmetric key schemes or public key schemes.

At step 518, the storage services 116 stores the encrypted code and pseudonym in the database 124 as code data 120.

At step 520, the integration engine 114 works with the storage services 116 to use the extracted metadata at step 504 to map incoming data stream to enterprise ontology for semantic mapping. Semantic mapping is accomplished through a combination of schema or metadata obtained from step 504, ontology that has been created and updated by the IoT server 112, and understanding of semantic distance or semantic similarity of data. The semantic mapper present in storage services 116 dynamically builds a semantic model with new or updated data sources by applying machine learning algorithms to cluster and classify incoming new schema. Based on metadata of the record, the integration engine semantically maps incoming contents to enterprise ontology thereby lending itself to contextual search by authorized or secondary users of the data.

The process 500 in FIG. 5 highlights how collected data from connected or IoT devices are handled. Member data may be added or updated using the process 500, and member data may be removed from database 124 by removing a member profile from the IoT server 112. When adding member data, the integration engine 114 collects all metadata including member preferences, access permissions and privacy controls. As each data is processed, if any PHI or PII elements are present in the data, member-identifiable and medical data are separated. The storage services 116 then pseudonomizes member-identifiable data, generates a code to link member-identifiable, medical and metadata for future access and stores all parts of the collected data (metadata, member-identifiable and medical) in the database 124. The link code acts as a key to access pseudonym which in turn will be used to access actual member data. Additionally, the storage services 116 in conjunction with the integration engine 114 will read the metadata, find appropriate semantic mapping based on enterprise ontology and update semantics of the ontology. A new node will be added if metadata contains new semantic element. For example, if metadata "number of weekly allergic reactions" was never present in the enterprise ontology and the collected data includes this metadata, the enterprise ontology will be updated to include this new semantic element.

The use of the enterprise ontology allows for updating data within database 124 when new collected data arrives for a specific member. The IoT server 112 verifies from metadata the type of data that is being updated. If the member and the type of data already exist in the database 124, the storage services 116 will override existing data with incoming data depending on type of data in the content that is being added. In some embodiments, overriding involves removing an existing record and adding a new record. Therefore, the storage services 116 will delete the record and follow the same process 500 as that of adding member data to create pseudonyms, to separate member-identifiable from medical data, and to update the database 124 with everything relating to incoming data (metadata, member-identifiable and medical data).

The use of code links, tokens or pseudonyms, and member linked storage allows for removing data from database 124. When a member is removed from the IoT server 112, IoT server 112 will get access to member data and initiate clearing member data from the database 124.

Once member data is securely stored in database 124, database 124 may hold data for one or more members. These members' data may be made available to authorized users, for example, those identified by items 102, 104, 106, and 108 in FIG. 1. FIGS. 6-9 provide embodiments of making data of one or more members available to an authorized user. The procedures of re-identification and de-identification of the stored data in database 124 may be performed to have the data available while at the same time protecting member privacy.

Figure 6:
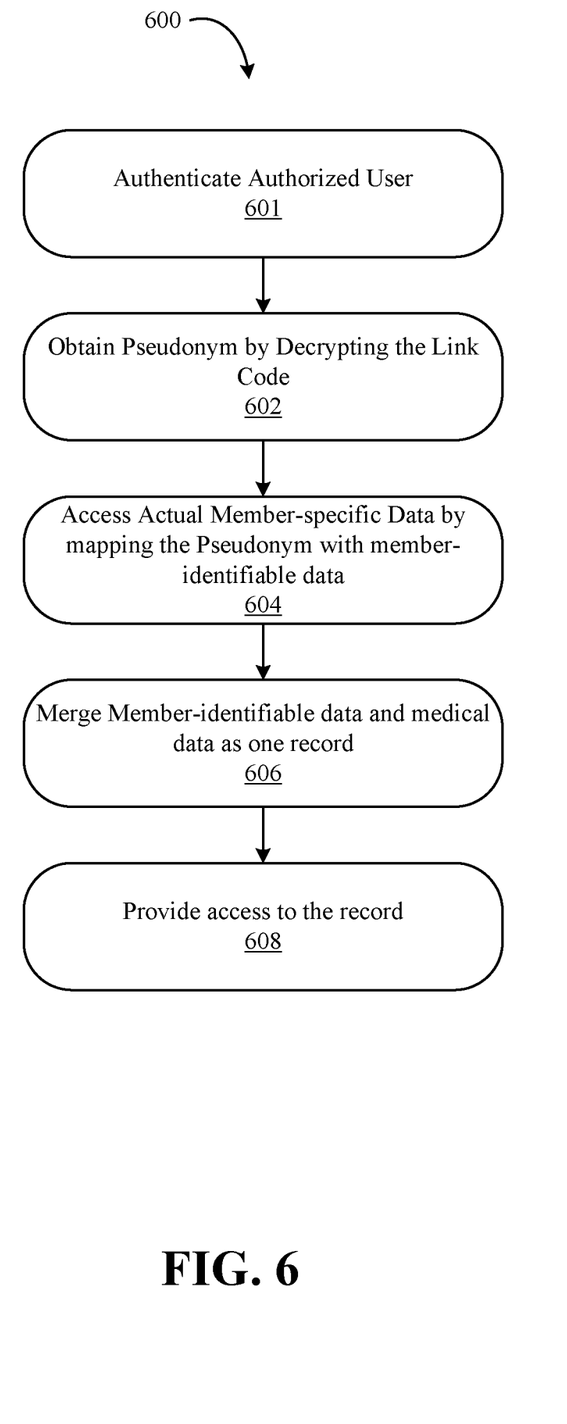
FIG. 6 shows a flow diagram illustrating the steps of providing member data according to an embodiment of the disclosure.

FIG. 6 shows a flow diagram illustrating the steps taken by an IoT server 112 to provide access to member health oriented data according to an embodiment of the disclosure. At step 601, the integration engine 114 authenticates a user to make sure that the user is an authorized user.

At step 602, the storage services 116 of the IoT server 112 obtains the pseudonym by decrypting the link code. Using the authorized user's credentials, the storage services 116 gets access to the link code in order to access member data. Afterward, the link code is used to access the pseudonym of the data. For example, a symmetric key may be used to decrypt the code data 120 in order to identify the pseudonym.

At step 604, the storage services 116 of the IoT server 112 accesses actual member-specific data by mapping the pseudonym in the pseudonymized member-identifiable data with the member-identifiable data. The IoT server 112 uses the pseudonym to access medical data in medical data 118 and also uses the same pseudonym to access member-identifiable data in user data 122. Using the map function from the user data 122, the storage services 116 maps the pseudonym to the member-identifiable data.

At step 606, the storage services 116 merges the member-identifiable data and the medical data as one record.

At step 608, the integration engine 114 provides, for example, a user device 110-3, access to the record via the storage services 116.

In FIG. 6, a registered member 102 may request access to data from his/her client device 110 through, for example, a web portal. In some cases anyone 104 (Parent, Guardian, relative or a friend) that the registered member has provided authorization to access his/her data including member-identifiable fields during emergency may request access. Healthcare providers 106 may also request access to provide care for the registered member. Once a request is received, the IoT server 112 will first verify credentials to make sure the requestor is authenticated to access entire data including member-identifiable data. The IoT server 112 will then perform the de-pseudonymization step 602 to then re-identify member data (both member-identifiable and medical data) at steps 604 and 606, and then disseminate the contents of the data to the requestor at step 608.

Figure 7:
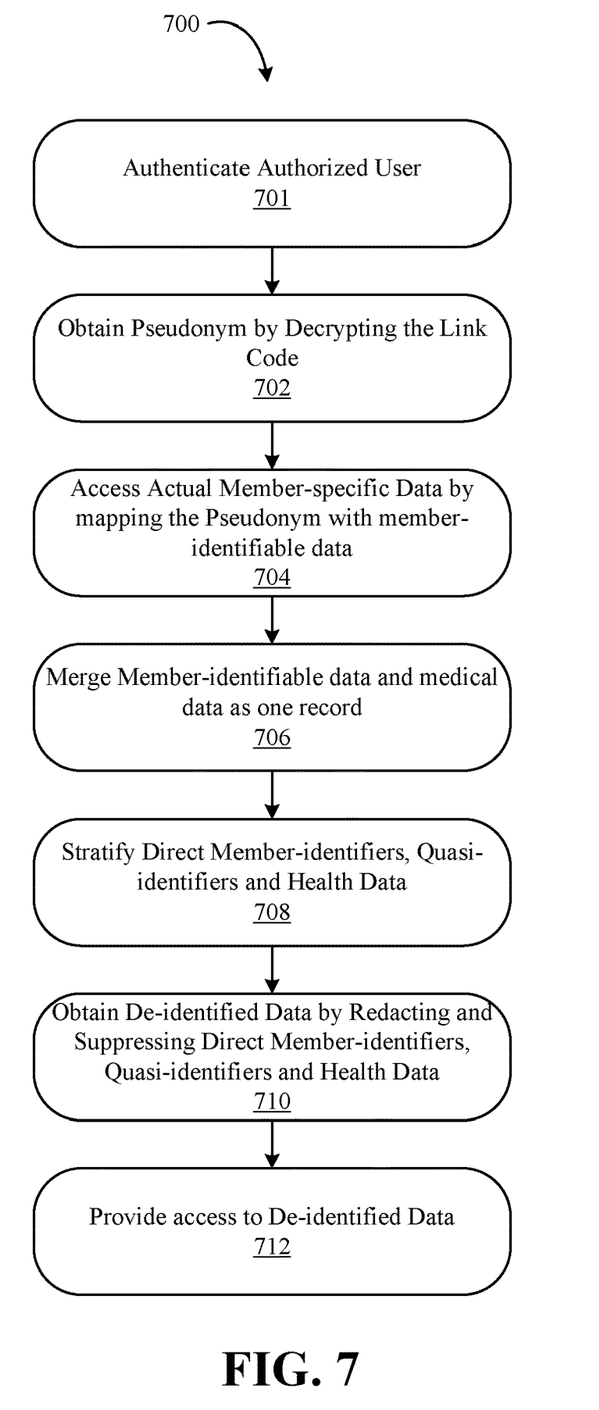
FIG. 7 shows a flow diagram illustrating the steps of providing de-identified data according to some embodiments of the disclosure.

FIG. 7 shows a flow diagram illustrating the steps taken by an IoT server 112 to provide de-identified member data to a client device 110 according to some embodiments of the disclosure. Steps 701, 702, 704, and 706 correspond to similar steps 601, 602, 604, and 606 in FIG. 6. At step 701, the integration engine 114 authenticates a user to make sure that the user is an authorized user. At step 702, the storage services 116 of the IoT server 112 obtains the pseudonym by decrypting the link code. At step 704, the storage services 116 of the IoT server 112 accesses actual member-specific data by mapping the pseudonym in the pseudonymized member-identifiable data with the member-identifiable data. At step 706, the storage services 116 merges the member-identifiable data and the medical data as one record.

At step 708, the storage services 116 stratifies direct member-identifiers, quasi-identifiers, and health or medical data. Direct member-identifiers are identifiers that directly distinguish the member, for example, SSN, patient ID, member ID, name, address, etc. Quasi-identifiers are identifiers that may be shared by more than a handful of individuals, for example, locations (such as, zip codes, hospital names, regions), age, dates (such as, birth, death, admission, discharge, visit, and specimen collection), race and ethnicity, languages spoken, profession, gender, weight (at admission, at discharge, at birth), and so on. Quasi-identifiers do not directly identify a member but rather are background information in the data that can seldom be used by hackers to identify actual member through correlations with other data.

At step 710, the storage services 116 obtains de-identified data by redacting and suppressing direct member-identifiers, quasi-identifiers, and health data. Examples of how this is accomplished is provided in FIG. 9 for various identifiers and health data.

At step 712, the integration engine 114 provides a third-party device 110-4 access to the record via the storage services 116.

In FIG. 7, a secondary party 108, for example, clinical, population health or any other medical researcher, may request access to member data for analysis. The IoT server 112 will first check if the secondary party 108 has authentication and authorization to access just medical data or medical data combined with a de-identified form of some of the member-specific data. The process 700 starts with applying de-pseudonymization steps 702 and re-identification steps 704 and 706. Once member data has been re-identified, the IoT server 112 will check member's preferences to find out authorized level of access to data. For example, two levels of access may exist, a first level providing access just medical data or a second level providing access to anonymized details about members in addition to the medical data. Depending on the credentials of the secondary party 108 and the preferences of the member, the IoT server 112 will intelligently apply de-identification algorithms (steps 708 and 710) and provision data for secondary usage at step 712.

Figure 8:
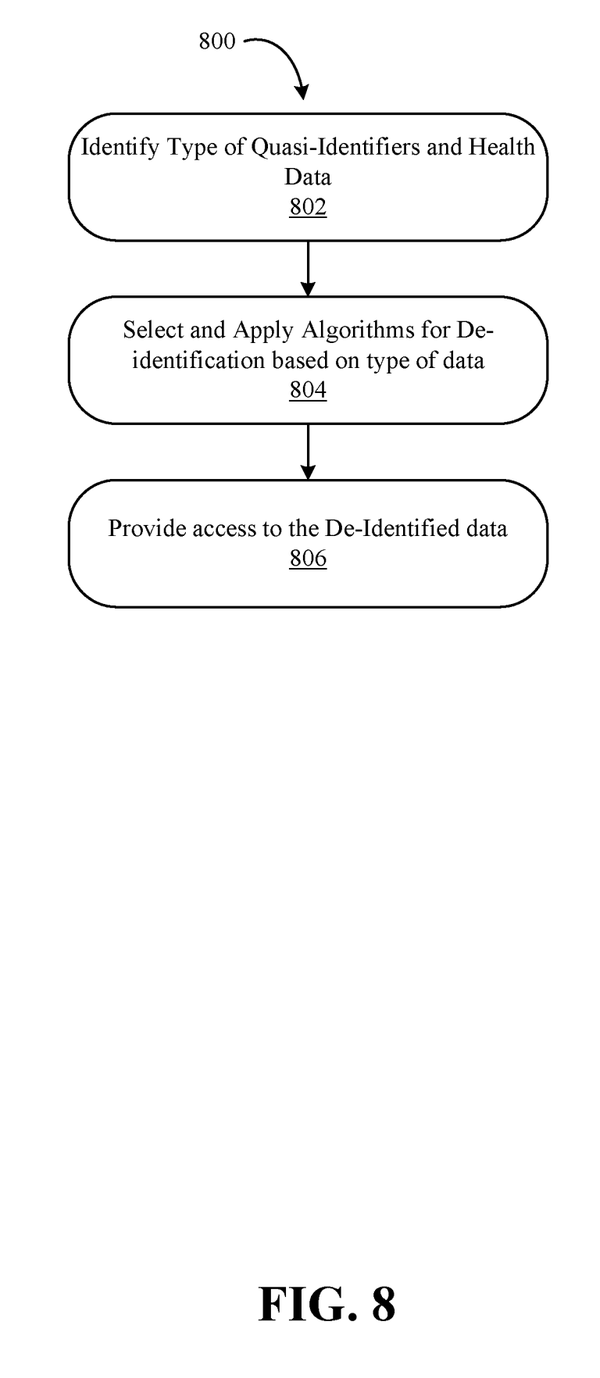
FIG. 8 shows a flow diagram illustrating the steps of de-identifying data according to some embodiments of the disclosure.

FIG. 8 shows a flow diagram illustrating the steps taken by IoT server 112 to de-identify data according to some embodiments of the disclosure. The flow diagram in FIG. 8 illustrating the de-identification process 800 is an embodiment of step 710. At step 802, the IoT server 112 identifies the type of member-identifiers, quasi-identifiers, and health data. These identifiers include, for example, SSN, member name, member address, member DOB, handwritten notes about the member, member zip code, member's age, when and where data was obtained, medical codes applying to procedures a member has undergone, and so on.

Figure 9:
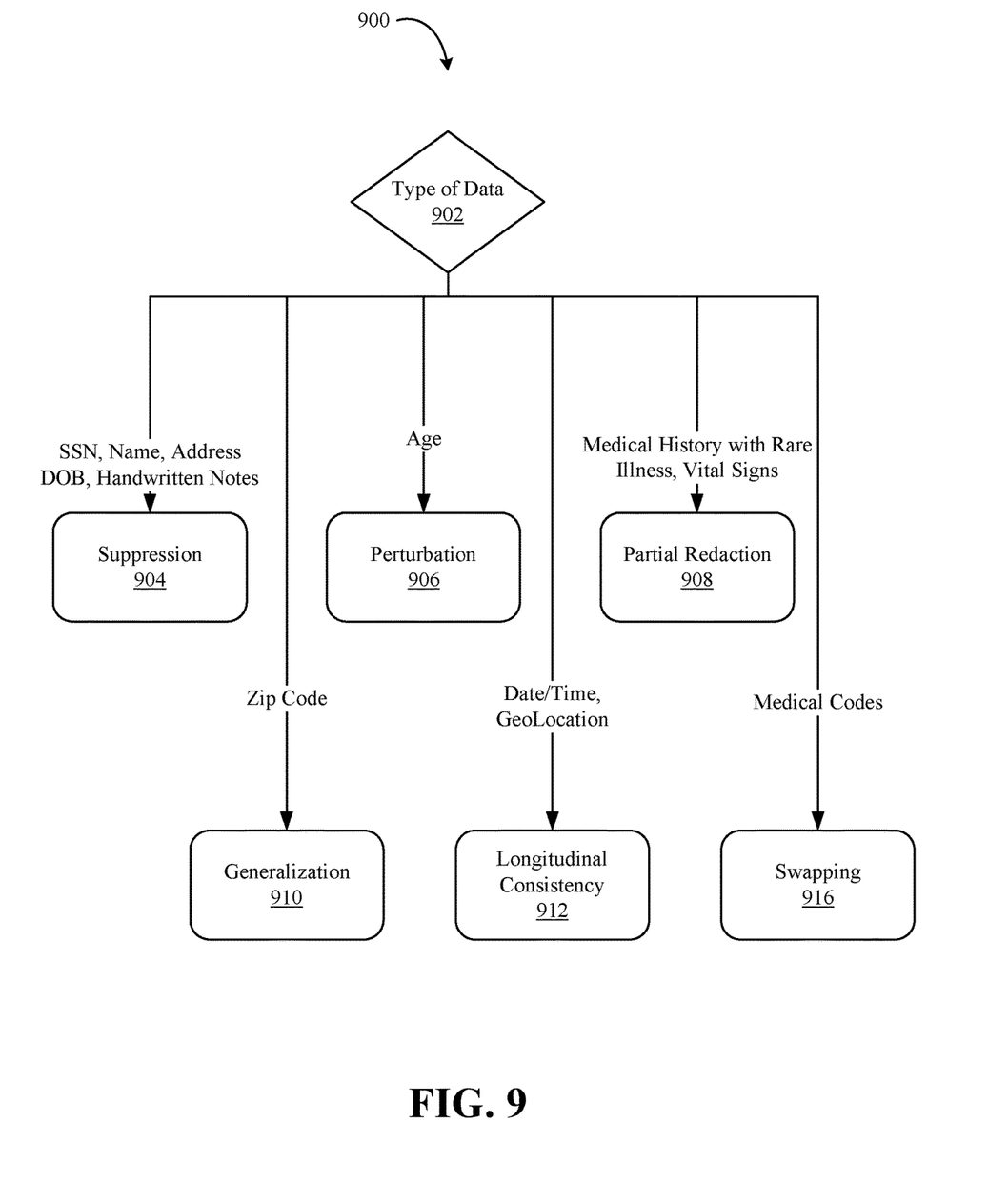
FIG. 9 shows a flow diagram identifying algorithms for de-identifying data according to some embodiments of the disclosure.

At step 804, based on the type of identifier, the storage services 116 selects an algorithm for de-identification and applies the selected algorithm to the data characterized by the type of identifier to obtain the de-identified data. FIG. 9 provides an example embodiment of algorithms to use based on types of identifiers.

At step 806, the IoT server 112 provides access to the de-identified data. Step 806 is analogous to step 712.

FIG. 9 shows a flow diagram illustrating steps taken by the IoT server 112 to select algorithms for de-identifying data according to some embodiments of the disclosure. At step 902, the storage services 116 of the IoT server 112 determines the type of data. The type of data is determined based on quasi-identifiers, health data, or member-identifiers.

At step 904, if the type of data is an SNN, member's name, member's address, member's DOB, or handwritten notes, then the algorithm chosen by the storage services 116 is a suppression algorithm. Suppression involves completely removing data with wild characters, such as, asterisk (*), number sign (#), etc., or with a NULL symbol. For example, patient name and SSN are removed with wild characters for all purposes of secondary use.

At step 906, if the type of data is the member's age, then the algorithm chosen by the storage services 116 is a perturbation algorithm. Perturbation involves falsifying data by purposefully introducing an element of error. This may be accomplished by introducing multiplicative or additive noise to data. For example, a patient's age may be reported as a random value within a 5-year window of the actual age. Another example is perturbing a patient's zip code by adding or subtracting +/−3 from the original zip code.

At step 908, if the type of data is the member's medical history with a rare illness or the member's vital signs, then the algorithm chosen by the storage services 116 is a partial redaction algorithm. For example, the system may determine which parts of the data to partially redact by comparing information in medical data against a list of rare illnesses from the National Institute of Health (NIH) Genetic and Rare Diseases Information Center (GARD). If a rare disease is the list from NIH GARD matches an item in the member's medical history, that item may be partially redacted.

At step 910, if the type of data is the member's zip code, then the algorithm chosen by the storage services 116 is a generalization algorithm. Generalization transforms data into more abstract representation to reduce granularity of data. For example, a five-digit zip code may be generalized to a four-digit zip code, which in turn may be generalized to a three-digit zip code, and onward so as to disclose data with lesser degrees of granularity. In another example, the age of a patient may be generalized into groups, for instance, age 40 can be generalized into "Between 35 and 44" and similarly, age 16 can be generalized as "Under 21."

At step 912, if the type of data is data specifying date and/or time and geolocation, then the de-identifying algorithm chosen by the storage services 116 is longitudinal consistency algorithm.

At step 916, if the type of data is a medical code, then the de-identifying algorithm chosen by the storage services 116 is a swapping algorithm.

One example to demonstrate how the system in FIG. 1 may be used is provided. A blood sugar level monitoring device may supply data collected from a patient or member to the integration engine 114. After cleansing and tokenizing the data, the storage services 116 will apply data protection techniques—separate member-identifiable data and medical data (blood sugar level data points in this case), apply pseudonymization to the member-identifiable data, and store both pieces of data encrypted in database 124. Additionally, the storage services 116 will update enterprise ontology based on metadata (such as type of data and actual device name) obtained from incoming data. Updating enterprise ontology helps to provide semantic mapping and linkage of data with other contents already stored in the database 124.

Four types of consumers can access the data: an owner who is supplying blood sugar level data from his/her connected device, healthcare provider who views recent blood sugar levels to treat the owner's or patient's diabetes, authorized user of data such as the owner's relative or friend who is allowed to access complete medical data of the owner under emergency conditions when the owner is not in a position to access the data, and clinical researcher or population health analyst who wants to access medical data and de-identified member data for analysis purposes. Member (data owner), healthcare provider and member-authorized users are considered primary users, and clinical researcher and population health analyst are considered secondary users. Note that, the secondary users do not have complete access to owner or member data unlike primary users.

When a primary user requests access to the member's data, the member's data in the database 124 is re-identified for plaintext display by de-pseudonymizing member-identifiable data and merging the member-identifiable data with medical data as one record. On the other hand, when a secondary user accesses the same blood sugar level data, depending on the member's preferences as to whether his/her data is allowed for access by secondary users, the storage services 116 applies appropriate algorithms to de-identify member-identifiable data, merge the member-identifiable data with medical data and provision to a clinical researcher or population health analyst. Note that, the member (data owner) can update preferences at any time to modify access to authorized users as well as level of access to his/her data for secondary users.

Embodiments of the disclosure provide methods of managing risk exposure of a member-identified data fields. The "Integrating the Health Enterprise (IHE) IT Infrastructure Handbook" by the IHE IT Infrastructure Technical Committee, which is incorporated in its entirety by reference, provides examples of member-identifiable data fields and risk exposure of these fields. Additionally, the IHE IT Infrastructure Handbook includes multiple approaches to de-identification of different types of data.

Embodiments of the disclosure provide competitive advantages to organizations and enterprises. Organizations may enjoy improved customer satisfaction and loyalty, reduced member attrition, and increased revenue since members will have an increased trust about the security of their data from connected devices used throughout the day. Customers will know that by using automated de-identification, their health data is not compromised.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for aggregating and providing health data records to an electronic device, the method performed by a server comprising a processor and a non-transitory computer readable medium with processor-executable instructions stored thereon, such that when the instructions are executed by the processor, the server performs the method comprising:
   receiving collected data from one or more client devices, the collected data, associated with a plurality of member profiles, comprising health related data including at least one of step count data, heart rate data, or sleep sensor data;
   extracting metadata from the collected data to obtain extracted metadata;
   separating member-identifiable data and medical data in the collected data in response to protected health information and personal identifiable information being present in the collected data;
   pseudonymizing the collected data;
   categorizing the collected data by mapping the extracted metadata to an enterprise ontology of the server;
   determining whether the metadata contains a new semantic element;
   updating the enterprise ontology with a new node when the metadata contains a new semantic element;

determining whether the type of collected data was previously stored for the associated member profile, wherein the type of collected data is a node in the enterprise ontology;
when the type of collected data was previously stored for the associated member profile, removing an existing record containing the previously stored collected data;
storing the collected data separately as the extracted metadata, the member-identifiable data, and the medical data, with the member-identifiable data decoupled from the medical data;
authenticating the electronic device;
receiving a request from the electronic device to access the collected data;
determining whether the electronic device is a secondary party as defined a first member profile in the plurality of member profiles and whether the electronic device is a secondary party as defined in a second member profile in the plurality of member profiles;
determining whether the secondary party has authorization to access only medical data when the electronic device is a secondary party as defined in the second member profile or has authorization to access a curated combination of member-identifiable data and medical data when the electronic device is a secondary party as defined in the first member profile;
providing the curated combination of member-identifiable data and medical data associated with the first member profile to the electronic device, when the secondary party has authorization to access a curated combination of member-identifiable data and medical data; and
providing only medical data associated with the second member profile to the electronic device when the secondary party has authorization to access only medical data.

2. The method according to claim 1, wherein the receiving collected data from the client devices comprises at least one of:
receiving collected data in real-time from the client devices;
receiving collected data in batch from an intermediary;
receiving collected data after a data threshold has been surpassed; and
receiving collected data after a certain amount of time has elapsed.

3. The method according to claim 1,
wherein member-identifiable data comprises protected health information and personal identifiable information, and medical data comprises doctor's notes, clinical notes, diagnostic results, vital sign readings, or radiology images.

4. The method according to claim 3, wherein the pseudonymizing the collected data comprises performing the following steps for each member profile in the plurality of member profiles:
creating, for a respective member profile, a pseudonym using a cryptographic algorithm;
encrypting the pseudonym;
creating a map function to access member-identifiable data associated with the respective member profile through the pseudonym;
linking medical data associated with the respective member profile with the pseudonym;
generating a code to link the member-identifiable data associated with the respective member profile and the medical data associated with the respective member profile; and
encrypting the code.

5. The method according to claim 4, wherein storing the collected data comprises storing the collected data for each member profile in the plurality of member profiles by:
storing, for a respective member profile, the map function and the member-identifiable data paired with the pseudonym in a database;
storing, for the respective member profile, the medical data paired with the pseudonym in the database; and
storing, for the respective member profile, the encrypted code paired with the pseudonym in the database.

6. The method according to claim 1, wherein pseudonymizing the collected data comprises performing the following steps for each member profile in the plurality of member profiles:
creating, for a respective member profile, a pseudonym using a cryptographic algorithm;
encrypting the pseudonym; and
creating a map function to access collected data associated with the respective member profile through the pseudonym.

7. The method according to claim 1, further comprising:
determining that the electronic device is a primary device associated with a third member profile in the plurality of member profiles;
re-identifying, in the pseudonymized collected data, only pseudonymized collected data associated with the third member profile to obtain a health data record associated with the third member profile, the health data record comprising both the member-identifiable data associated with the third member profile and the medical data associated with the third member profile; and
providing the health data record associated with the third member profile to the electronic device.

8. The method according to claim 7, wherein the re-identifying comprises:
obtaining a pseudonym for the third member profile by decrypting a link code for the third member profile;
accessing actual member-specific data associated with the third member profile by mapping the pseudonym with the member-identifiable data of the third member profile; and
merging the member-identifiable data associated with the third member profile and the medical data associated with the third member profile to obtain the health data record associated with the third member profile.

9. The method according to claim 1, further comprising:
de-identifying data in a health data record associated with the first member profile to obtain a de-identified health data record associated with the first member profile; and
providing the de-identified health data record to the electronic device.

10. The method according to claim 9, wherein the de-identifying comprises:
stratifying direct member-identifiers, quasi-identifiers, and the medical data associated with the first member profile;
obtaining the de-identified health data record associated with the first member profile by determining a type of direct member-identifier, quasi-identifier, and medical data and applying a de-identification algorithm based on the type of direct member-identifier, quasi-identifier, and medical data, wherein the de-identification algorithm obscures values related to the member-identifier, quasi-identifier and/or medical data.

11. The method according to claim 10, wherein the de-identification algorithm is selected from the group consisting of:
suppression; generalization; perturbation; longitudinal consistency; partial redaction; redaction; and swapping.

12. A server for aggregating and providing health data records to an electronic device, the server comprising a processor and a non-transitory computer readable medium with processor-executable instructions stored thereon, such that when the instructions are executed by the processor, the server performs the method comprising:
receiving collected data from one or more client devices, the collected data, associated with a plurality of member profiles, comprising health related data including at least one of step count data, heart rate data, or sleep sensor data;
extracting metadata from the collected data to obtain extracted metadata;
separating member-identifiable data and medical data in the collected data in response to protected health information and personal identifiable information being present in the collected data;
pseudonymizing the collected data;
categorizing the collected data by mapping the extracted metadata to an enterprise ontology of the server;
determining whether the metadata contains a new semantic element;
updating the enterprise ontology with a new node when the metadata contains a new semantic element;
determining whether the type of collected data was previously stored for the associated member profile, wherein the type of collected data is a node in the enterprise ontology;
when the type of collected data was previously stored for the associated member profile, removing an existing record containing the previously stored collected data;
storing the collected data separately as the extracted metadata, the member-identifiable data, and the medical data, with the member-identifiable data stored at a higher level of security;
authenticating the electronic device;
receiving a request from the electronic device to access the collected data;
determining whether the electronic device is a secondary party as defined a first member profile in the plurality of member profiles and whether the electronic device is a secondary party as defined in a second member profile in the plurality of member profiles;
determining whether the secondary party has authorization to access only medical data when the electronic device is a secondary party as defined in the second member profile or has authorization to access a curated combination of member-identifiable data and medical data when the electronic device is a secondary party as defined in the first member profile;
providing the curated combination of member-identifiable data and medical data associated with the first member profile to the electronic device, when the secondary party has authorization to access a curated combination of member-identifiable data and medical data; and
providing only medical data associated with the second member profile to the electronic device when the secondary party has authorization to access only medical data.

13. The server according to claim 12, wherein the receiving collected data from the client devices comprises at least one of:
receiving collected data in real-time from the client devices;
receiving collected data in batch from an intermediary;
receiving collected data after a data threshold has been surpassed; and
receiving collected data after a certain amount of time has elapsed.

14. The server according to claim 12,
wherein member-identifiable data comprises protected health information and personal identifiable information, and medical data comprises doctor's notes, clinical notes, diagnostic results, vital sign readings, or radiology images.

15. The server according to claim 14, wherein the pseudonymizing the collected data comprises performing the following steps for each member profile in the plurality of member profiles:
creating, for a respective member profile, a pseudonym using a cryptographic algorithm;
encrypting the pseudonym;
creating a map function to access member-identifiable data associated with the respective member profile through the pseudonym;
linking medical data associated with the respective member profile with the pseudonym;
generating a code to link the member-identifiable data associated with the respective member profile and the medical data associated with the respective member profile; and
encrypting the code.

16. The server according to claim 14, wherein storing the collected data comprises storing the collected data for each member profile in the plurality of member profiles by:
storing, for a respective member profile, the map function and the member-identifiable data paired with the pseudonym in a database;
storing, for the respective member profile, the medical data paired with the pseudonym in the database; and
storing, for the respective member profile, the encrypted code paired with the pseudonym in the database.

17. The server according to claim 12, wherein pseudonymizing the collected data comprises performing the following steps for each member profile in the plurality of member profiles:
creating, for a respective member profile, a pseudonym using a cryptographic algorithm;
encrypting the pseudonym; and
creating a map function to access collected data associated with the respective member profile through the pseudonym.

18. The server according to claim 12, further performing the method comprising:
determining that the electronic device is a primary device associated with a third member profile in the plurality of member profiles;
re-identifying, in the pseudonymized collected data, only pseudonymized collected data associated with the third member profile to obtain a health data record associated with the third member profile, the health data record comprising both the member-identifiable data associated with the third member profile and the medical data associated with the third member profile; and
providing the health data record associated with the third member profile to the electronic device, wherein re-identifying comprises: (a) obtaining a pseudonym for the third member profile by decrypting a link code for the third member profile, (b) accessing actual member-specific data associated with the third member profile by mapping the pseudonym with the member-identifiable data of the third member profile, and (c) merging the member-identifiable data associated with the third member profile and the medical data associated with the third member profile to obtain the health data record associated with the third member profile.

19. The server according to claim 12, further performing the method comprising:
   de-identifying data in a health data record associated with the first member profile to obtain a de-identified health data record associated with the first member profile; and
   providing the de-identified health data record to the electronic device,
   wherein the de-identifying comprises: (a) stratifying direct member-identifiers, quasi-identifiers, and the medical data associated with the first member profile, and (b) obtaining the de-identified health data record associated with the first member profile by determining a type of direct member-identifier, quasi-identifier, and medical data and applying a de-identification algorithm based on the type of direct member-identifier, quasi-identifier, and medical data, wherein the de-identification algorithm obscures values related to the member-identifier, quasi-identifier and/or medical data.

20. A non-transitory computer-readable medium for aggregating and providing health data records to an electronic device, the non-transitory computer-readable medium storing processor-executable instructions for performing the method comprising:
   receiving collected data from one or more client devices, the collected data, associated with a plurality of member profiles, comprising health related data including at least one of step count data, heart rate data, or sleep sensor data;
   extracting metadata from the collected data to obtain extracted metadata;
   separating member-identifiable data and medical data in the collected data in response to protected health information and personal identifiable information being present in the collected data;
   pseudonymizing the collected data;
   categorizing the collected data by mapping the extracted metadata to an enterprise ontology of the server;
   determining whether the metadata contains a new semantic element;
   updating the enterprise ontology with a new node when the metadata contains a new semantic element;
   determining whether the type of collected data was previously stored for the associated member profile, wherein the type of collected data is a node in the enterprise ontology;
   when the type of collected data was previously stored for the associated member profile, removing an existing record containing the previously stored collected data;
   storing the collected data separately as the extracted metadata, the member-identifiable data, and the medical data, with the member-identifiable data decoupled from the medical data;
   authenticating the electronic device;
   receiving a request from the electronic device to access the collected data;
   determining whether the electronic device is a secondary party as defined a first member profile in the plurality of member profiles and whether the electronic device is a secondary party as defined in a second member profile in the plurality of member profiles;
   determining whether the secondary party has authorization to access only medical data when the electronic device is a secondary party as defined in the second member profile or has authorization to access a curated combination of member-identifiable data and medical data when the electronic device is a secondary party as defined in the first member profile;
   providing the curated combination of member-identifiable data and medical data associated with the first member profile to the electronic device, when the secondary party has authorization to access a curated combination of member-identifiable data and medical data; and
   providing only medical data associated with the second member profile to the electronic device when the secondary party has authorization to access only medical data.

* * * * *